US00PP25281P3

(12) United States Plant Patent
Tsukahara

(10) Patent No.: US PP25,281 P3
(45) Date of Patent: Feb. 3, 2015

(54) ***PETUNIA* PLANT NAMED 'PBLLV40-0'**

(50) Latin Name: ***Petunia* hybrid**
Varietal Denomination: PBLLV40-0

(71) Applicant: Jun Tsukahara, Fukuoka (JP)

(72) Inventor: Jun Tsukahara, Fukuoka (JP)

(73) Assignee: Suntory Flowers Limited (JP)

( * ) Notice: Subject to any disclaimer, the term of this patent is extended or adjusted under 35 U.S.C. 154(b) by 211 days.

(21) Appl. No.: 13/815,141

(22) Filed: Jan. 31, 2013

(65) Prior Publication Data

US 2014/0215671 P1 Jul. 31, 2014

(51) Int. Cl.
*A01H 5/00* (2006.01)

(52) U.S. Cl.
USPC ..... Plt./356.12

(58) Field of Classification Search
USPC ..... Plt./356.1, 356.12
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'PBLLV40-0' is disclosed, characterized by unique, fully double green-white flowers. The new variety is a *Petunia*, suitable as an outdoor garden or container plant.

2 Drawing Sheets

Figure 1:
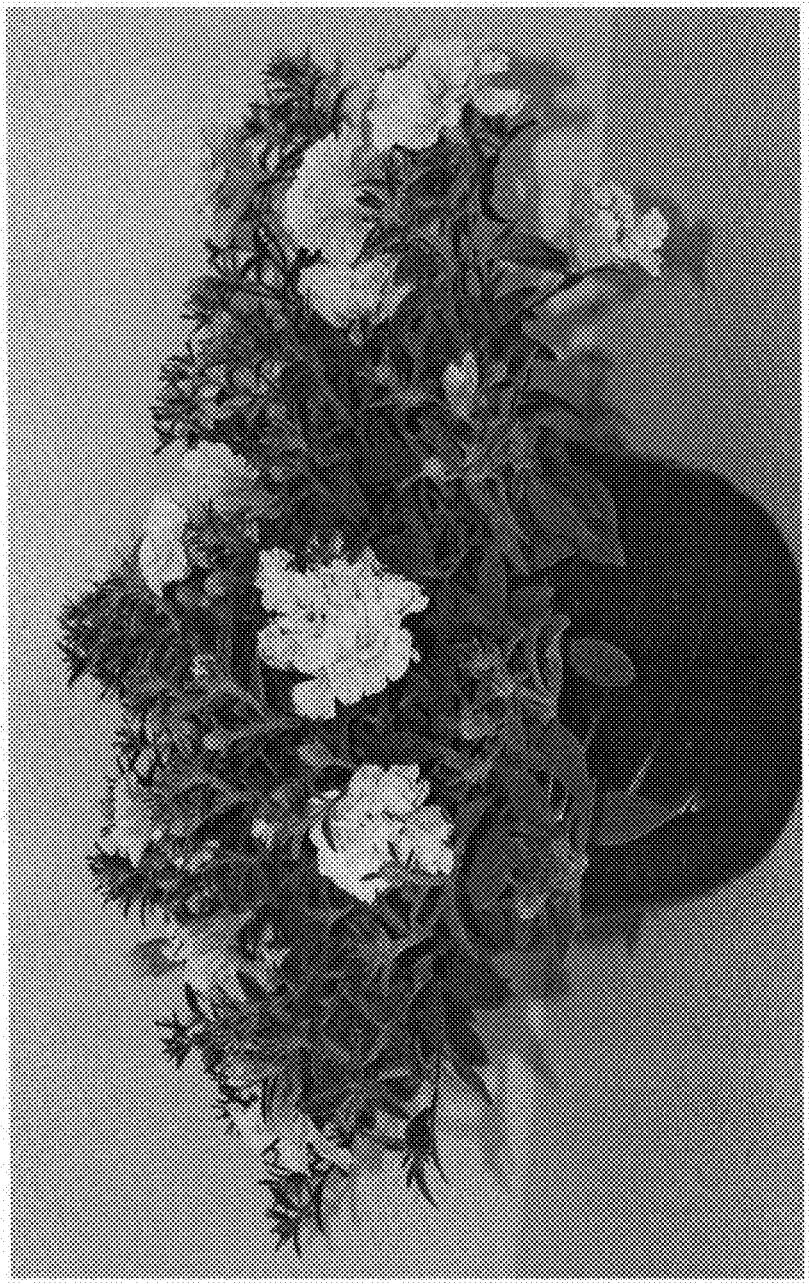

Latin name of the genus and species: *Petunia* hybrid.
Variety denomination: 'PBLLV40-0'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September of 2008. The new variety was discovered in May of 2009 by the inventor in a group of seedlings resulting from that crossing, in a research greenhouse in Yame, Fukuoka, Japan.

Asexual reproduction of the new cultivar 'PBLLV40-0' by vegetative cuttings was first performed at a research greenhouse in Yame, Fukuoka, Japan in September of 2009. Subsequently one generation has been produced and has shown that the unique features of this cultivar are stable and reproduced true to type.

SUMMARY OF THE INVENTION

The cultivar 'PBLLV40-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PBLLV40-0.' These characteristics in combination distinguish 'PBLLV40-0' as a new and distinct *Petunia* cultivar:

1. Unique green-white colored double flower.
2. Very compact growth habit
3. High flower count.

COMPARISON TO THE PARENT VARIETIES

Plants of the new cultivar 'PBLLV40-0' are similar in most horticultural characteristics to plants of the unnamed proprietary seed parent. However, the new cultivar produces a pale greenish yellow double flower whereas the seed parent produces a pale yellow single flower. Additionally, plants of new cultivar produces a larger flower and a shorter length stem compared to those of the seed parent.

Plants of the new cultivar 'PBLLV40-0' are similar in most horticultural characteristics to plants of the unnamed proprietary pollen parent. However, plants of the pollen parent produce pale yellow colored flowers that are larger than the pale greenish yellow flowers of the new cultivar. The new cultivar also produces a longer peduncle than the pollen parent.

COMPARISON TO COMMERCIAL VARIETIES

The new cultivar can be compared to the patented commercial variety 'Daiichi Bluette Purple2' U.S. Plant Pat. No. 22,236. 'PBLLV40-0' is similar to this commercial variety in most horticultural characteristics, most specifically, in plant habit, however, plants of the new cultivar produce pale yellowish green colored flowers, whereas flower of 'Daiichi Bluette Purple2' bright reddish purple. Additionally the new cultivar produces a double flower form compared to the single flower form of 'Daiichi Bluette Purple2'.

The new cultivar can be compared to the patented commercial variety 'PDBVI35-0', U.S. Plant Pat. No. 22,985. 'PBLLV40-0' is similar to this commercial variety in most horticultural characteristics, most specifically, in plant habit, and both varieties have unique double flowers. However, plants of the new cultivar produce pale yellowish green colored flowers, compared to the dark purple colored flowers of 'PDBVI35-0'.

BRIEF DESCRIPTION OF THE PHOTOGRAPHS

The accompanying photograph in FIG. 1 illustrates in full color a typical plant of 'PBLLV40-0' grown in a greenhouse, in a 10 inch commercial basket. Age of the plant photographed is approximately 20 weeks from 5 rooted cuttings.

Figure 2:
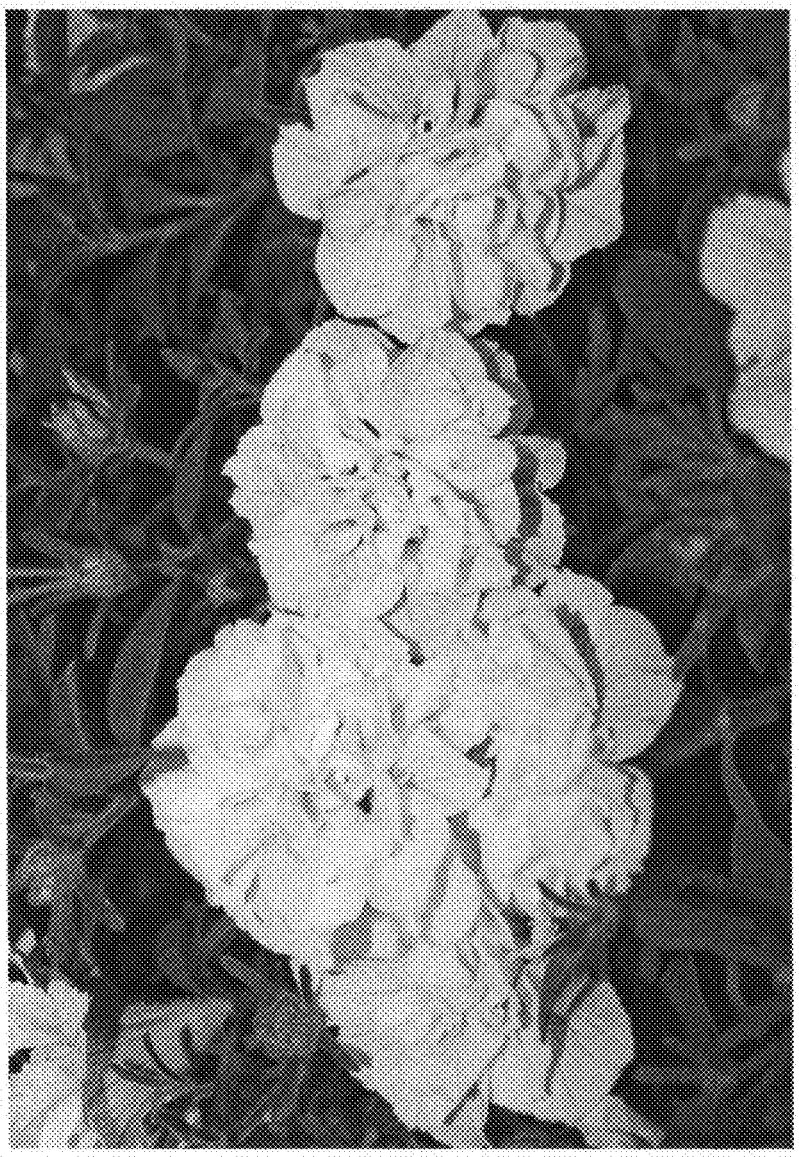

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'PBLLV40-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types. Botanical classification: *Petunia* hybrid 'PBLLV40-0'.

PROPAGATION

Time to initiate roots: About 7 days at approximately 25° C.
Time to develop roots: About 14 to 21 days at approximately 25° C.
Root description: Fine, fibrous.

PLANT

Growth habit: Mounding and trailing.
Age of the plant described: Approximately 20 weeks from 5 rooted cuttings.
Pot size of plant described: Approximately 10 inch basket.
Height: Approximately 19 cm from soil line to top of plant.
Plant spread: Approximately 50 cm at widest point.
Growth rate: Rapid.
Branching characteristics: Free branching.
Length of primary lateral branches: Approximately 12 cm.
Quantity of primary lateral branches: Approximately 60.
Characteristics of primary lateral branches:
- *Diameter*.—Approximately 0.4 cm.
- *Color*.—Near RHS Yellow-Green 144B.
- *Texture*.—Pubescent. Slightly sticky.
- *Strength*.—Highly flexible, very strong.

Internode length: Average 1.1 cm.

FOLIAGE

Leaf:
- *Arrangement*.—Opposite.
- *Quantity*.—Approximately 20 per main lateral branch.
- *Average length*.—Approximately 6.0 cm.
- *Average width*.—Approximately 2.5 cm.
- *Shape of blade*.—Obovate.
- *Apex*.—Acute.
- *Base*.—Obtuse.
- *Margin*.—Entire.
- *Texture of top surface*.—Matte with pubescence.
- *Texture of bottom surface*.—Matte with pubescence.
- *Pubescence*.—Very short, less than 1 mm hairs, densely covering leaf.
- *Aspect*.—Slightly arched.
- *Color*.—Young foliage upper side: Near RHS Green 137C. Young foliage under side: Near RHS Green 137C. Mature foliage upper side: Near RHS Green 137A. Mature foliage under side: Near RHS Green 137C.
- *Venation*.—Type: Pinnate. Venation color upper side: Near RHS Yellow-Green 144B. Venation color under side: Near RHS Yellow-Green 144B.
- *Petiole*.—Length: Approximately 0.7 cm. Diameter: Approximately 0.1 cm. Color: Near RHS Yellow-Green 144B. Texture: Pubescent.

FLOWER

Natural flowering season: Spring and Summer.
Days to flowering from rooted cutting: Approximately 50.
Inflorescence and flower type and habit: Singly occurring at leaf axils, fully double flowers with fused petals.
Rate of flower opening: Approximately 4 to 5 days from bud to fully opened flower.
Flower longevity on plant: Approximately 1 week.
Approximate quantity of flowers per plant: Approximately 150 flowers and buds.
Flowers persistent:
- *Bud*.—Shape: Elongated sphere. Length: Approximately 2.2 cm. Diameter: Approximately 1.4 cm. Color: Near RHS Yellow-Green 145B.
- *Flower size*.—Diameter: Approximately 5.9 cm. Depth: Approximately 3.5 cm. Flower measurements: Individual tube not measurable because filled with petals. Petal Quantity: Approximately 20, irregularly sized and fused.
- *Petals*.—Width: Range from 1.5 to 4.0 cm. Length: Range from 1.5 to 2.5 cm. Quantity: 20, fused. Texture: Smooth. Aspect: Ruffled. Apex: Truncate. Margin: Small, irregular dentations.
- *Color*.—When opening: Inner surface: Near RHS Green-White 157C, Yellow-Green 144D at base. Faint veins near Yellow-Green 144C. Outer surface: Near RHS Green-White 157C, Yellow-Green 144D at base. Veins near Yellow-Green 144C. Fully opened: Inner surface: Near RHS Green-White 157D, Yellow-Green 154B and 154C at base and flush through center of petal. Faint veins near Yellow-Green 144C. Outer surface: Near RHS Green-White 157D, Yellow-Green 150C and 150D at base and flush through center of petal. Veins near Yellow-Green 144C. Petal color, fading to: Inner surface: Near White 155D, veins year Green-Yellow 1A. Outer surface: Near RHS Yellow 4D.
- *Calyx/sepals*.—Quantity per flower: 5, fused at base. Shape: Lanceolate. Length: Approximately 2.1 cm. Width: Approximately 0.4 cm. Apex: Acute. Base: Fused. Margin: Entire. Texture: Pubescent. Color: Upper Surface: Near RHS Green 138A. Lower Surface: Near RHS Green 138B.
- *Peduncle*.—Length: Approximately 2.5 cm. Diameter: Approximately 0.3 cm. Color: Near RHS Green 143B. Orientation: Approximately 25 degree angle from stem.
- *Fragrance*.—Musty.

REPRODUCTIVE ORGANS

Stamens:
- *Number*.—Approximately 20, some deformed.
- *Filament length*.—Average 1.3 cm.

Anthers:
- *Length*.—Approximately 0.1 cm.
- *Shape*.—Oblate.
- *Color*.—RHS Greyed-Yellow 161C.
- *Pollen*.—Not observed.

Pistil: Deformed mass, no detectable Gynoecium.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° C. to 35° C.

What is claimed is:

1. A new and distinct cultivar of *Petunia* plant named 'PBLLV40-0' as herein illustrated and described.

* * * * *